United States Patent [19]

Friesen et al.

[11] Patent Number: 5,484,722
[45] Date of Patent: Jan. 16, 1996

[54] BIOPOLYMER AND EFFECTOR SUBSTANCE CONJUGATES, PROCESS FOR THE PREPARATION THEREOF AND THEIR USE

[75] Inventors: Heinz-Jürgen Friesen; Peter Hermentin, both of Marburg, Germany

[73] Assignee: Behringwerke Aktiengesellschaft, Marburg, Germany

[21] Appl. No.: 201,209

[22] Filed: Feb. 24, 1994

Related U.S. Application Data

[62] Division of Ser. No. 549,102, Jul. 6, 1990, Pat. No. 5,321,142.

[30] Foreign Application Priority Data

Jul. 10, 1989 [DE] Germany .......................... 39 22 608.5

[51] Int. Cl.⁶ .............................. C12N 9/96; C07K 16/00
[52] U.S. Cl. .................. 435/188; 530/391.5; 530/391.9; 530/404
[58] Field of Search ........................ 435/188; 530/391.5, 530/391.9, 404, 806

[56] References Cited

U.S. PATENT DOCUMENTS 4,868,106  9/1989  Ito et al. .................................. 436/518

FOREIGN PATENT DOCUMENTS 0175459  10/1984  Japan .

OTHER PUBLICATIONS

M. Augustin et al., Journal f. prakt. Chemie., vol. 327, No. 5, pp. 857–864 (1985).
Keller et al., "Preparation and Some Properties of Maleimido Acids and Maleoyl Derivatives of Peptides", Helvetica Chimica Acta, 58(2):531–541 (1975).
Rich et al., "Alkylating Derivatives of Amino Acids and Peptides. Synthesis of N–Maleoylamino Acids, [1–(N–Maleoylglycyl)cysteinyl]oxytocin, and [1–(N–Maleoyl–11–aminoundecanoyl)cysteinyl]oxytocin. Effects on Vasopressin–Stimulated Water Loss from Isolated Toad Bladder", J. Med. Chem., 18:1004–1010 (1975).
Anderson et al., "The Use of Esters of N–Hydroxysuccinimide in Peptide Synthesis", J. Am. Chem. Soc., 86:1839–1842 (1964).
Ghose et al., "Preparation of Antibody–Linked Cytotoxic Agents", Methods in Enzymology, 93:280–333 (1983).
Ishikawa et al., "Enzyme Labeling of Antibodies and Their Fragments for Enzyme Immunoassay and Immunohistochemical Staining", J. Immunoassay, 4(3):209–237 (1983).

Primary Examiner—Mary E. Ceperley
Attorney, Agent, or Firm—Finnegan, Henderson, Farabow, Garrett & Dunner

[57] ABSTRACT

The invention relates to compounds from biopolymers and effector substances which are linked with the aid of derivatives of optically active amino acids in which the amino group has been converted into a maleimido group and the carboxyl group into an active ester group, processes for the preparation thereof and the use thereof.

4 Claims, No Drawings

BIOPOLYMER AND EFFECTOR SUBSTANCE CONJUGATES, PROCESS FOR THE PREPARATION THEREOF AND THEIR USE

This is a division of application Ser. No. 07/549,102, filed Jul. 6, 1990, now U.S. Pat. No. 5,321,142.

The invention relates to compounds from biopolymers and effector substances which are linked with the aid of derivatives of optically active amino acids in which the amino group has been converted into a maleimido group and the carboxyl group into an active ester group.

Conjugates which can be prepared from biopolymers such as peptides or proteins and marker or effector substances or specific binding partners by covalent chemical linkage are needed in the diagnostic and therapeutic field. Preferred methods which are employed in these couplings are those in which the specific properties of the components to be linked to each other are not changed at all or else are changed in a defined way by the coupling. A summary of known methods for the preparation of protein conjugates from the field of enzyme immunoassays is given in a review article by Ishikawa et al. (J. Immunoassay 24 (1983) 209–327). Methods for the preparation of immunotoxins are, for example, listed in a review article by Ghose et al. (Methods in Enzymology, Vol. 93 (1983) pp. 280–333). Processes for the preparation of conjugates using heterobifunctional reagents make possible the specific controlled linkage of the coupling partners. In the case of protein conjugates, methods in which linkages of SH groups with amino groups are established play an important role because of the low risk of side reactions if the reaction is carried out in a proper way. Cross-linking reagents having maleimido, haloalkyl or haloacyl and active ester structures are preferably used in this case.

The cross-linking reagents which have been described so far were not suitable, since they have no chiral carbon atom in the bridge, for the formation of conjugates with a defined chiral structure in the bridge. Moreover, it has not been possible in the case of cross-linking reagents having a short-chain bridging component to suit the polarity of the cross-linking agent to the particular conditions required.

The object on which the present invention is based was now to provide conjugates from biopolymers and effector substances, which are important for diagnosis and therapy, in a sterically defined form, it being necessary to suit the cross-linking reagent, with respect to length, mobility and polarity, to the optimum coupling conditions for the components to be coupled. Furthermore, the bridges formed during coupling are to be of sufficient stability and, if appropriate, cleavable in a predetermined fashion.

The present invention now relates to compounds of the formula I

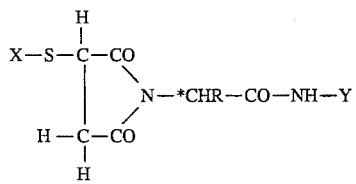

in which

*C is an asymmetric carbon atom, R is the side chain of a natural amino acid, of methionine sulfone or of cysteic acid, X is the radical of the thiol coupling component and Y represents the radical of the amino coupling component.

Compounds in which the thiol coupling component X—SH and the amino coupling component Y—NH$_2$ are each proteins are preferred here.

Compounds in which

X—SH is an enzyme, an antibody or a fragment of an antibody and

Y—NH$_2$ is an enzyme, an antibody or a fragment of an antibody are particularly preferred.

Compounds in which the enzyme is peroxidase, β-galactosidase or phosphatase, and the antibodies or the fragments of antibodies are derived from rabbits, sheep, goats or mice, are very particularly preferred, antibodies or fragments of antibodies against CEA, AFP, HCG, TSH and HBsAg being particularly preferred.

Compounds in which R is the side chain of the amino acid alanine, of methionine sulfone or of cysteic acid, and very particularly preferably of the amino acid alanine are furthermore preferred.

The invention also relates to a process for the preparation of a compound according to formula I, in which process an amide is formed in a first reaction step by reacting an amino component Y—NH$_2$ with the functional active ester group of a compound of the formula II

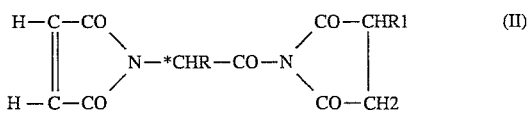

in which *C is an asymmetric carbon atom, R has the meaning stated for formula I and R$^1$ is hydrogen or a radical of the formula III

in which R$^3$ is hydrogen or C$_1$ to C$_4$ alkyl, and a thioether is formed in a second reaction step by Michael addition, by reacting a thiol component X—SH with the maleimido group of the compound of the formula II.

The invention further relates to compounds of the formula II in which R and R$^1$ have the meanings stated therefor.

Compounds preferred in this case are those in which R corresponds to the side chain of the amino acid alanine, of methionine sulfone or of cysteic acid, and very particularly of the amino acid alanine.

The invention also relates to the use of compounds according to formula I for analysis, diagnosis or therapy. The use in an enzyme immunoassay is preferred in this connection.

The invention finally relates to the use of a compound according to formula II for the preparation of a compound of the formula I.

For the preparation of the linker reagents according to formula II, maleimido groups are formed, for example by processes known to those skilled in the art, by reacting primary amino groups with maleic anhydride and cyclizing the maleoyl derivatives formed with the elimination of water to give maleimido derivatives (maleoyl derivatives) (Keller and Rudinger (1975); Helvetica Chimica Acta 58, 531–541 and Rich et al. (1975); J. Med. Chem. 18, 1004–1010).

The N-hydroxysuccinimide or sulfo-N-hydroxysuccinimide ester groups are formed, for example, from the carboxyl groups and N-hydroxysuccinimide or the sulfone derivative thereof with the elimination of water and with the aid of reagents such as carbodiimides (Anderson et al. (1964); J. Am. Chem. Soc. 86, 1839 et seq.).

If the side chains R contain groups which undergo side reactions under the conditions for formation of the maleimido group or the active ester groups, appropriate substitutions or modifications must be carried out there to prevent these side reactions. In reagents derived from the amino acid methionine, the oxidation-sensitive thioether functionalities are, for example, converted into sulfone groups which, in addition, bring about better solubility in water of the resulting compound. In the case of cysteine, a SH-protecting group which is readily soluble in water, such as the acetamidomethyl (Acm) protective group, is, for example, employed, or, even more advantageously, an oxidation of the SH group to give a sulfonic acid group with the formation of cysteic acid which, as the sulfonic acid salt, can be employed for the synthesis of the corresponding heterobifunctional reagent. In the case of lysine or ornithine, it is preferred to use polar, acid-stable amino-protective groups such as the methylsulfonyloxycarbonyl (Msc) group as the protein-modification reagents. If appropriate, the protective group for the amino acid side chain is selected such that, after linking the first two coupling partners, the protective groups on the side chain can be eliminated without destroying the properties of the coupling partners required for the application. The use of the Msc protective group as aminoprotective group or of the thiopyridyl radical for the protection of thiol are examples. Both protective groups can be removed in many cases of protein-protein conjugates without harming the proteins. In the case of protection of thiol, the liberated thiol functionality can be used for introducing a third coupling component.

The compounds according to formula II can be employed for the preparation of conjugates by methods known to those skilled in the art. A survey of methods for the preparation of protein conjugates in the field of enzyme immunoassays is, for example, given in the review article by Ishikawa et al. (J. Immunoassay 4 (1983) 209–327). Methods for the preparation of immunotoxins are, for example, listed in the review by Ghose et al. (Methods of Enzymology, vol. 93 (1983) pp. 280–333).

Reagents which contain a chiral carbon atom in the bridge between the two functional groups have not been described for use in immunoassays. A derivative containing the structure —CH(CH$_3$)—CO— in the bridge presents itself as the simplest member of this series. Such a reagent containing maleimido and succinimide ester or sulfosuccinimide ester groups is, as expected, readily soluble in water because of the small hydrophobic portion in the molecule. It can be prepared from the amino acid alanine as described above.

Reagents with the structure II can advantageously be used for linking immunoglobulins and marker enzymes for immunoassays.

In this case, thiol groups can for example be introduced into the immunoglobulin (Ishikawa et al., 1983), maleimido groups can be introduced into the marker enzyme by reacting the amino groups of the enzyme and, after the removal of excess reagents, the modified immunoglobulin can be reacted with the modified enzyme for coupling.

In another way of carrying out the reaction, maleimido groups can be introduced by reacting the amino groups of the immunoglobulin with reagents of the structure II and can be reacted with thiol groups already present in the marker enzyme (e.g. β-galactosidase from *E. coli*). or with thiol groups which have been introduced by reaction with reagents such as 2-iminothiolane, for coupling.

The conjugations can be carried out in a particularly specific fashion with respect to the binding site and also to stoichiometry if the hinge thiols in Fab' of immunoglobulins are reacted with maleimido groups in the enzyme which can be obtained by reacting the enzyme with reagents of the structure II. The coupling of the enzyme is then carried out on the end of the Fab' opposite the paratope. In an analogous case, thiol groups can be generated by reducing agents in the hinge region of immunoglobulins and can be reacted with the maleimido groups of the enzyme. It was surprising that the amino groups of one protein could be readily linked with the SH groups of the amino acid cysteine in the other protein in view of the short length and low flexibility in the bridging component of the cross-linking reagents.

The examples which follow are intended to illustrate the preparation of compounds of the structure II and the use thereof for the preparation of compounds of the structure I.

EXAMPLE 1

Preparation of maleoyl-L-alanine

L-alanine (26.7 g; 0.30 mol) is added to a stirred solution of maleic anhydride (29.4 g; 0.30 mol) in glacial acetic acid (300 ml). After stirring for 3 hours, the reaction product is filtered off, dried and recrystallized from acetone/hexane. Further crystals can be obtained on concentrating the mother liquor. The total yield is 33 g (60%). The melting point of the product is 142–144 degree C.

EXAMPLE 2

Preparation of maleoyl-L-alanine

Maleoyl-L-alanine (4 g; 21 mmol) is suspended in dry toluene (150 ml), triethylamine (4 ml) is added and the mixture is then boiled, with stirring, for 6 h under reflux with a water trap. The hot solution is then decanted off the orange colored residue and, after cooling, is concentrated to dryness in a rotary evaporator. 50 ml of water which has been adjusted to pH 3 with hydrochloric acid are added to the viscous residue which is extracted 5 times at pH 3 with 50 ml of ethyl acetate in each case, readjusting the pH each time. The combined ethyl acetate phases are concentrated to dryness in a rotary evaporator and the solid product obtained is dried overnight under high vacuum. Yield: 1.25 g $^1$H-NMR (200 MHz, CDCl$_3$; TMS): δ 1.65 (d, 3H, I=7.4 Hz, CH$_3$), 4.82 (q, 1H, I=7.4 Hz, CH), 6.74 (s, 2H, maleimido), 8.30 (bs, COOH).

EXAMPLE 3

Preparation of maleoyl-L-alanine-N-hydroxysuccinimide ester (MAS)

Maleoyl-L-alanine (200 mg; 1.2 mmol) and N-hydroxysuccinimide (150 mg; 1.3 mmol) are dissolved in tetrahydrofuran. A solution of dicyclohexylcarbodiimide (255 mg; 1.2 mmol) in tetrahydrofuran (1 ml) is added dropwise and while stirring to the solution which has been cooled to 0° C., and stirring is continued at 4° C. overnight. The resulting suspension is filtered off and the filtrate is concentrated to dryness in a rotary evaporator. The residue is resuspended in 2 ml of tetrahydrofuran and the suspension is filtered through a P4 glass frit. The filtrate is concentrated to dryness in a rotary evaporator and the solid product obtained is dried under high vacuum.

Yield: 330 mg $^1$H-NMR (200 MHz, CDCl$_3$; TMS): δ1.77 (d, 3H, I=7.4 Hz, CH$_3$), 2.84 (s, 4H, succinimidyl) 5.17 (q, 1H, I=7.4 Hz, CH), 6.80 (s, 2H, maleimido).

EXAMPLE 4

Preparation of a maleimido-antibody a) Reagents

MAS which has been prepared according to Example 3 is used; boric acid (E. Merck, order No. 165); dioxane (E. Merck, order No. 3110); lithium hydroxide (E. Merck, order No. 11652).

b) Preparation of solutions

Lithium borate buffer, pH 8.5

Boric acid (1.24 g) is stirred in a mixture of water (80 ml) and dioxane (20 ml). The pH is adjusted to 8.5 by the addition of solid lithium hydroxide while dissolving the boric acid.

MAS solution

MAS (0.0124 g) is dissolved in dioxane (1 ml).

Phosphate buffer pH 6.0

Sodium dihydrogen phosphate monohydrate (41.4 g) and Titriplex (5.58 g) are dissolved in water (3 l). The pH is adjusted to 6.0 with sodium hydroxide solution.

c) Preparation of the maleimido-antibody

The antibody to be conjugated (concentration 4 g/l in 1/15 M phosphate-buffered physiological saline, 25 ml) is mixed with lithium borate buffer (25 ml). 0.45 ml of MAS solution (corresponding to a 30-fold molar excess of MAS over IgG) is added to the resulting solution having a pH of 7.5, while stirring. After incubation at room temperature for 1 hour, the excess reagents are removed by gel filtration on a Sephadex G-25 column equilibrated with phosphate buffer, pH 6.0.

EXAMPLE 5

Preparation of a thiol-peroxidase a) Reagents

Peroxidase (degree of purity I, Boehringer Mannheim, order No. 815462), 2-iminothiolane hydrochloride (Sigma, order No. 6256), methanol (E. Merck, order No. 6009), disodium tetraborate decahydrate (E. Merck, order No. 6308)

b) Solutions

Sodium borate solution

Disodium tetraborate (0.952 g) is dissolved in water (100 ml).

Iminothiolane solution

2-Iminothiolane (0.688 g) is dissolved in methanol (5 ml).

c) Preparation of the thiol-peroxidase

Peroxidase (160 mg) is dissolved in sodium borate buffer and mixed with iminothiolane solution. After incubation of the reaction mixture at room temperature for 2 hours, the excess reagents are removed by gel chromatography on a Sephadex G-25 column equilibrated with phosphate buffer, pH 6.0 (Example 4, section b)).

EXAMPLE 6

Preparation of a peroxidase/antibody conjugate a) Reagents

Maleimido-antibody and thiol-peroxidase according to Example 4) and Example 5), TRIS (E. Merck, order No. 9382).

b) Solutions

TRIS buffer, pH 7.4

TRIS (18.17 g) is dissolved in water (3 l) and the pH is adjusted to 7.4 with HCl.

c) Preparation of the peroxidase/antibody conjugate

Maleimido-antibody solution and thiol-peroxidase solution are mixed corresponding to a molar ratio of antibody to peroxidase of 1:5. After incubation at room temperature for 2 hours, the reaction is stopped by addition of 1/10 volumes of NEM solution. Excess reagents are removed after incubation for 30 minutes by gel chromatography on a Sephadex G-25 column which has been equilibrated with TRIS buffer.

d) Properties of the conjugate

No remaining free antibody is detected on HPLC analysis by gel chromatography on a DuPont GF-250 column. A molar ratio of peroxidase to antibody of 2.5±0.5 on comparison of various preparations with polyclonal antibodies is found in the conjugate peak by optical analysis. In the case of monoclonal antibodies, the molar ratio can vary in the range from 1.5 l to 3.5 l. The conjugate can be used directly for the enzyme immunoassay in the dilution used specifically for the particular assay.

Fractionation of the conjugate by gel chromatography improves the specific reaction of the conjugate in a few cases.

EXAMPLE 7

Preparation of a maleimido-peroxidase a) Reagents and solutions

N-Ethylmorpholine, 98% pure (Riedel de Haen, order No. 62050), N,N-dimethylformamide (Riedel de Haen, order No. 15440), all other reagents and solutions as in Examples 4–6.

b) Preparation of the maleimido-peroxidase

Peroxidase (1 g) is dissolved in water (6.5 ml). Dioxane (3.5 ml) is mixed into this solution. The pH is adjusted to 8.5 with ethylmorpholine. This solution is mixed with a solution of MAS (24 mg) in dimethylformamide (0.5 ml). After incubation at room temperature for 1 hour the buffer is changed to phosphate buffer, pH 6.0, by gel filtration on Sephadex G-25.

EXAMPLE 8

Preparation of Fab'—SH

Fab' with free SH groups in the hinge region is prepared by known methods (Ishikawa et al. (1983) J. Immunoassay 4, 209–327). For this, IgG is cleaved to give F(ab')$_2$ using pepsin. The disulfide bridges of the hinge in the F(ab')$_2$ are reduced to thiols by thiol/disulfide exchange using mercaptoethylamine. The reaction mixture is freed of excess thiol and the buffer is changed to phosphate buffer, pH 6.0 by gel filtration.

EXAMPLE 9

Preparation of a Fab'/peroxidase conjugate

Fab'—SH according to Example 8 (100 mg in 20 ml of phosphate buffer, pH 6.0) is mixed with maleimido-peroxidase according to Example 7 (500 mg in 10 ml of phosphate buffer, pH 6.0) and the mixture is incubated at 37 degrees Celsius for 1 hour. The conjugate formed is separated from the remaining Fab'—SH and excess peroxidase by gel chromatography on Ultrogel ACA 44 (from Pharmacia). TRIS buffer, pH 7.4, is the eluent. In the case of rabbit antibodies, the main portion of the conjugate elutes corresponding to a 1+1 adduct of Fab' and peroxidase in the gel chromatography. The product can be used directly for the enzyme immunoassay in the dilution used specifically for the assay.

We claim:

1. A conjugate of the formula I

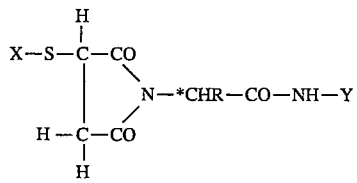

(I)

in which *C is an asymmetric carbon atom and R is the side chain of a natural amino acid, methionine sulfone or cysteic acid, X is the radical of the thiol coupling component of a protein and Y is the radical of the amino coupling component of a protein.

2. A conjugate as claimed in claim 1, in which X is an enzyme, an antibody or a fragment of an antibody and Y is an enzyme, an antibody or a fragment of an antibody.

3. A conjugate as claimed in claim 1, in which R denotes a side chain of the amino acid alanine, methionine sulfone or cysteic acid.

4. A conjugate as claimed in claim 3, in which R denotes a side chain of the amino acid alanine.

* * * * *